United States Patent
Michel

(10) Patent No.: US 6,736,795 B2
(45) Date of Patent: May 18, 2004

(54) DEVICE FOR ADMINISTERING AN INJECTABLE PRODUCT

(75) Inventor: Peter Michel, Burgdorf (CH)

(73) Assignee: Disetronic Licensing AG, Burgdorf (CH)

( * ) Notice: Subject to any disclaimer, the term of this patent is extended or adjusted under 35 U.S.C. 154(b) by 67 days.

(21) Appl. No.: 10/077,229

(22) Filed: Feb. 15, 2002

(65) Prior Publication Data

US 2002/0111589 A1 Aug. 15, 2002

Related U.S. Application Data

(63) Continuation of application No. PCT/CH00/00390, filed on Jul. 18, 2000.

(30) Foreign Application Priority Data

Aug. 18, 1989 (DE) .......................................... 199 39 023

(51) Int. Cl.[7] .............................................. A61M 37/00
(52) U.S. Cl. ...................................................... 604/131
(58) Field of Search ............................. 604/131, 93.01, 604/141, 142, 218, 236, 151, 152

(56) References Cited

U.S. PATENT DOCUMENTS 4,437,859 A  3/1984  Whitehouse et al.
5,788,673 A  8/1998  Young et al.

FOREIGN PATENT DOCUMENTS

DE  19614337 A1  8/1997
JP  5245197  9/1993

Primary Examiner—Manuel Mendez
(74) Attorney, Agent, or Firm—Dorsey & Whitney LLP

(57) ABSTRACT

The invention relates to a device for administering an injectable product, comprising:
 a) a casing (3);
 b) a container for said product accommodated by said casing (3)
 c) a delivering means (2) for delivering product out of said container (1);
 d) a drive means (8); and
 e) a transmission link via which said drive means (8) drives said delivering means (2).

The device is characterised in that:
 f) a fluid space (21, 22) for an incompressible fluid and
 g) a pressure reducing means (3, 10, 23) are provided in said transmission link;
 h) wherein said fluid space (21, 22) can be impinged on a drive side by pressure from said drive means (8) and said pressure reducing means (3, 10, 23) reduces a fluid pressure generated by said drive means (8) toward a driven side of said fluid space (21, 22).

22 Claims, 2 Drawing Sheets

Fig. 2 Detail I
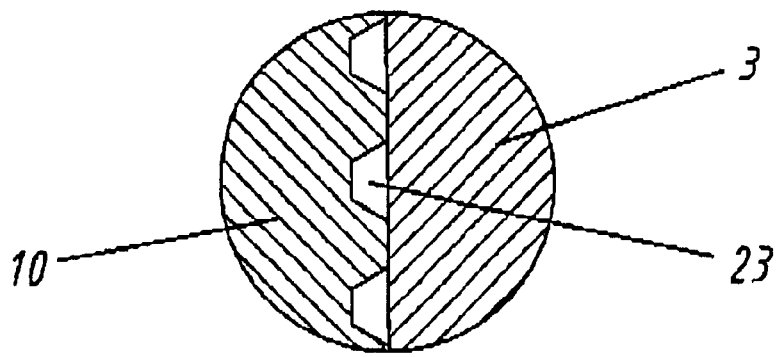
Fig. 3
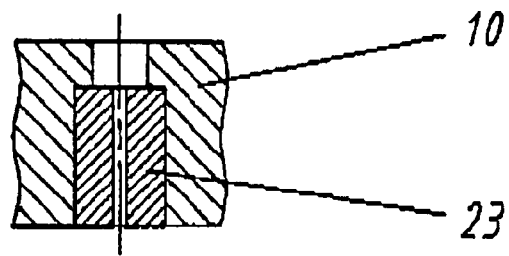

DEVICE FOR ADMINISTERING AN INJECTABLE PRODUCT

PRIORITY CLAIMS

This application is a Continuation of International Application No. PCT/CH00/00390, filed on Jul. 18, 2000, which claims priority to German Application No. DE 199 39 023 A1, filed on Aug. 18, 1999, both of which are incorporated herein by reference.

BACKGROUND OF THE INVENTION

1. Technical Field

The invention relates to a device for administering an injectable product.

2. Description of the Related Art

Injection devices, for example injection syringes or injection pens, such as the invention relates to in particular though not exclusively, conventionally comprise a casing which accommodates an ampoule with the product to be injected, a delivering means for delivering the product out of the ampoule and a coupling means. The delivering means is conventionally formed by a piston which is movable in the ampoule. In simple syringes, the muscular power of the user serves as the drive means. The use of spring elements, in particular pressure springs, as the drive means is also known. The coupling means forms a transmission link or drive connection from the drive means to the delivering means.

The known drive means, for example drive springs, have the disadvantage that the drive force or drive energy applied by them is subject to changes in the course of being released. In drive springs, the drive energy changes in accordance with the spring characteristic. The delivering rate of the delivering means follows such changes. Correspondingly, the delivery rate changes in the course of delivery in accordance with the changing drive energy.

SUMMARY OF THE INVENTION

It is an object of the invention to provide a device for administering an injectable product, with which the product is evenly delivered in the course of an injection or infusion.

The invention is based on a device for administering an injectable product which includes a casing, a container for the product accommodated by the casing, a delivering means, a drive means and a transmission link or coupling means. The product is delivered directly out of the container by the delivering means. The drive means supplies the drive energy required for this, said drive energy being transmitted in the transmission link to the delivering means, in such a way that the delivering means is driven by the drive means, to deliver the product.

The container, the delivering means, the drive means and the transmission members of the transmission link are preferably arranged in the casing. Other arrangements are, however, in principle equally possible. The injectable product is preferably a medical or cosmetic agent, in particular in the form of a liquid active solution. A prominent example is insulin, administered using the device within the context of a treatment for diabetes. The device is preferably an infusion device. It can, however, also be an injection device. The container can, in particular, be formed as an ampoule, as is the case in known infusion devices. The delivering means is preferably formed by a piston accommodated by the container, which is advanced towards an outlet of the container, to deliver the product. However, instead of such a piston, the delivering means can in principle be formed by any type of pump suitable for delivering the product.

According to its type, the drive means is preferably formed in such a way that it releases the energy stored in it when it is triggered. Via a coupling means, this released energy is transmitted in the transmission link to the delivering means which, driven for its part in this way, delivers the product out of the container. The drive means is preferably formed by a drive spring, particularly preferably a pressure spring. In principle, however, other designs of drive means may also be used, e.g. those which release a pressure gas when triggered.

According to the invention, a fluid space for an incompressible fluid and a pressure reducing means are provided in the transmission link from the drive means to the delivering means, i.e. in the coupling means.

The fluid space correspondingly comprises a drive side, upon which the drive means acts, and a driven side, which acts on the delivering means. Both the drive side and the driven side can be connected, directly or via other transmission members, to the drive means and/or delivering means respectively. The fluid space can be impinged on its drive side by pressure from the drive means. The pressure thus generated is reduced toward the driven side of the fluid space by the pressure reducing means. The pressure is preferably reduced to a fifth or less and particularly preferably to a tenth or less by means of the pressure reducing means. The pressure reducing means creates a fluid connection which only allows a delayed flow of the fluid from the drive side towards the driven side, such that in a dynamic state, i.e. while the delivering means is being driven, a greater fluid pressure prevails on the drive side than on the driven side.

The invention enables a drive means to be used in which substantially more energy is stored than would be required to drive the delivering means and the resulting delivery of the product. The comparatively large drive energy released when the drive means is triggered is attenuated by the fluid coupling in accordance with the invention onto the measure required for delivering and administering. The excess of drive energy is available, controlled due to the fluid coupling in accordance with the invention, for driving the delivering means. If a drive spring is used as the drive means, as is preferred, then the spring strength of this drive means can be significantly higher than in the case of a direct drive connection to the delivering means. In particular, such a drive spring can be operated in a smaller range of its spring characteristic than would be possible in the case of a direct coupling.

Particularly preferably, a working stroke of the drive means is transmitted into a working stroke of the delivering means by the fluid coupling, said working stroke of the delivering means being greater than the working stroke of the drive means. In the case of a pressure or tension spring as the drive means and a piston as the delivering means, the respective working stroke is the stretching or straining of the spring and the distance covered by the piston in dependence on this working stroke. Particularly preferably, the delivering means is formed as a piston and the drive means likewise acts on a piston, designated in the following as a drive piston. In this embodiment, the drive side of the fluid space is formed by a piston area of the drive piston. The piston area of the drive piston is preferably larger than a piston area of a driven piston, wherein the piston area of the driven piston forms the driven side of the fluid space.

Through this ratio of the two piston areas, a stroke of the drive piston is transmitted into a comparatively larger stroke of the driven piston. Expressed differently, a smaller stroke of the drive piston is required to achieve a given stroke of the driven piston. The working stroke of the drive piston can be kept correspondingly short. The drive means can be operated in a tight range around its optimal operating point. Furthermore, the different-sized piston areas lead to a reduction of force. The force exerted by the drive piston is reduced in accordance with the ratio of the areas of the drive piston and driven piston. This reduction occurs in addition to the reduction of force as a result of the reduction of pressure. The Applicant reserves the right to independently further prosecute the feature of the different-sized piston areas, together with features a) to e) of claim 1.

The driven piston can form the delivering means directly. The driven piston is, however, preferably another piston.

In a particularly preferred example embodiment, the fluid space is sub-divided into a first partial space including the drive side and a second partial space including the driven side, and the two partial spaces are connected to each other exclusively by a system of capillaries, if a higher pressure prevails on the drive side than on the driven side of the fluid space. The system of capillaries can be formed by a single capillary or also by a plurality of capillaries.

The capillary or plurality of capillaries is/are advantageously as long as possible. Its/their length is preferably at least 0.5 m. If a plurality of capillaries are formed, this preferably applies to each of the capillaries. The through-flow rate in long capillaries is less dependent on the diameter of the capillary, as directly follows from the Hagen-Poiseuille Law. According to the Hagen-Poiseuille Law, variations in the diameter due to imprecision in production enter into the through-flow rate in the fourth power. However, with an increasing length of the capillary, its diameter can likewise be enlarged, if the through-flow rate is to remain constant. Larger diameters are on the one hand by their very nature simpler to produce than smaller diameters, and with an increasing size of the diameter, deviations from the desired diameter arise to an increasingly less important extent only. Furthermore, an as high viscosity of the working fluid as possible in the fluid space is preferred.

The system of capillaries preferably comprises a capillary running spirally, or a plurality of such capillaries. In a preferred example embodiment, the system of capillaries is formed by a single, spiral capillary. A spiral capillary not only has the advantage of a large length, but can also be simply produced. In particular, it can be formed in the form of an external or internal thread on a corresponding surface area, preferably a shell or jacket surface area, of a capillary body. The capillary body with the external or internal thread is preferably placed into or onto another body with a smooth opposite surface area, wherein care must be taken that the threads of the capillary body are sealed against each other on the opposite surface area.

BRIEF DESCRIPTION OF THE DRAWINGS

The invention will now be described by way of a preferred example embodiment. There is shown:

FIG. 2 a capillary in accordance with Detail I of FIG. 1; and

FIG. 3 an alternative embodiment of a capillary.

DETAILED DESCRIPTION

Figure 1:
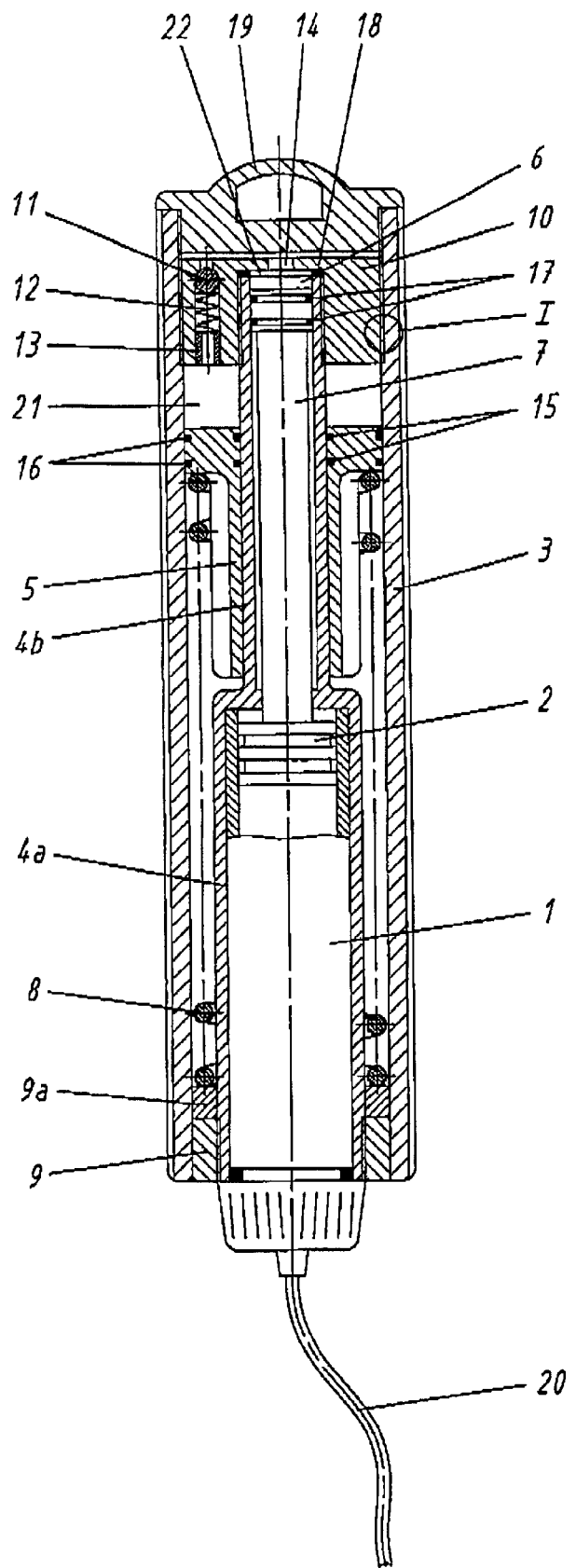
FIG. 1 an infusion device in a longitudinal section.

FIG. 1 shows a longitudinal section of an infusion device.

A circular cylindrical outer sleeve 3, together with a sealing piece 9 at a proximal end and a sealing cap 19 at a distal end, forms a casing of the infusion device. A container holder 4a is held centered in a proximal region of the outer sleeve 3. A container 1 in the form of an ampoule is accommodated by the container holder 4a, likewise centered with respect to the central longitudinal axis of the outer sleeve 3. The container 1 is filled with a product to be injected, for example insulin. A delivering means 2 in the form of a delivering piston is furthermore movably accommodated by the container, in a straight line toward an outlet of the container 1. A catheter 20 is connected to the outlet of the container 1 in a manner known in its own right.

An inner sleeve 4b is arranged in a distal region of the infusion device, concentric with respect to the outer sleeve 3. In the example embodiment, the container holder 4a and the inner sleeve 4b are formed as a one-piece sleeve. The container holder 4a and the inner sleeve 4b could also be separate components. However, forming them as one piece simplifies holding them commonly centered in the outer sleeve 3, as can be directly inferred from FIG. 1 and the subsequent description.

An inner surface area of the inner sleeve 4b forms a slide bearing for a driven piston 6 accommodated by the inner sleeve 4b, said driven piston being connected rigidly to the delivering piston 2 by means of a piston rod 7. The driven piston 6 and the piston rod 7 are formed as one piece. The piston rod 7 abuts the delivering piston 2. It could also be firmly connected to the delivering piston 2; for example, it could be screwed to the delivering piston 2. Furthermore, the piston rod 7 can equally be guided into a collar region between the container holder 4a and the inner sleeve 4b, for example guided fluid-proof. The driven piston 6 seals toward the inner sleeve 4b using sealing rings 17 in the manner of piston rings.

A ring space is formed between the outer sleeve 3 and the inner sleeve 4b, a drive piston 5 being arranged in said ring space. The drive piston 5 is a ring piston which is slid back and forth, fluid-proof and tight, between the outer sleeve 3 and the inner sleeve 4b. Sealing rings 15 are accommodated by grooves in an inner surface area of the drive piston 5 and other sealing rings 16 are accommodated by grooves on an outer surface area of the drive piston 5, each in the manner of piston rings. The drive piston 5 comprises a plane ring area on a distal front face. The drive piston 5 tapers toward the inner sleeve 4b in the proximal direction. The taper is formed by means of a collar. An opposite area of the infusion device lies opposite the collar, seen in the proximal direction. The opposite area is formed by a distance piece in the form of a distance ring 9a, which surrounds the container holder 4a and lies loose on the sealing piece 9.

In a ring space between the outer sleeve 3 on the one hand and the container holder 4a and the inner sleeve 4b on the other, a pressure spring 8 is accommodated between the two opposing areas, i.e. the collar of the drive piston 5 and the distance ring 9a, abutting the two areas. By varying the strength of the distance ring 9a, i.e. by exchanging it, the device can be simply adapted to different pressure springs 8, to continuously set the operative range of the spring optimally.

A capillary body 10 is arranged behind the drive piston 5 in the distal direction. The capillary body 10 comprises a proximal ring region and is occluded by a base at its distal end. In the region of its ring body, the capillary body 10 is sealed fluid-proof against the outer sleeve 3 and preferably also against the inner sleeve 4b. A distal front area of the inner sleeve 4b pushes fluid-proof against the base of the capillary body 10 via a sealing ring 18. The capillary body 10 is provided with a aperture opening 14 in the region of a distal opening on the front face of the inner sleeve 4b which is sealed by the sealing ring 18.

An aperture open in one direction only is formed in the capillary body 10 by a reflux valve. The reflux valve comprises a valve ball 11 which is pressed into its fitting within the capillary body 10 in a known way by means of a valve spring 12. The valve spring 12 is in turn supported on a valve closure 13.

A fluid space is formed between the distal front area of the drive piston 5 and a distal front area of the driven piston 6, said fluid space being occluded fluid-proof by said two pistons 5 and 6 and comprising a first partial space 21 and a second partial space 22. The two partial spaces 21 and 22 are separated from each other by the capillary body 10. The fluid space 21, 22 is completely filled with an incompressible working fluid. A highly viscous oil is preferably used as the working fluid.

The reflux valve 11, 12, 13 only allows a through-flow of the working fluid from the partial space 22 into the partial space 21, and prevents a through-flow in the other direction.

The capillary body 10, together with an inner surface area of the outer sleeve 3 surrounding the capillary body, forms a fluid connection in the form of a system of capillaries. The system of capillaries is shown in Detail I of FIG. 2. It is formed by a single, connected fluid channel, namely a capillary 23. The capillary 23, in the form of a multiple thread, encircles the outer surface area of the capillary body 10 in a spiral. In principle, the capillary 23 can also be formed by a single thread. When the capillary body 10 is installed, the capillary 23 connects the two partial fluid spaces 21 and 22. The inner surface area of the outer sleeve 3 opposite the capillary 23 is simply smooth. The capillary body 10 is guided into the outer sleeve 3 by a slight pressing power. When installed, the "teeth" on the outer surface area of the capillary body 10, which separate the individual threads of the capillary 23 from each other, press fluid-proof against the inner surface area of the outer sleeve 3. The teeth of the capillary body 10 are flattened for sealing purposes. The capillary body 10 consists of a softer material than the outer sleeve 3, in order to improve sealing. For the same purpose, however, the outer sleeve 3 could also in principle be made of a softer material than the capillary body 10.

An alternative embodiment of a capillary 23 is shown in FIG. 3. In this case, the capillary 23 is formed in one insert as a straight fluid channel. The insert is held fluid-proof in a receptacle of the capillary body. A bore which extends the capillary 23 of the insert is formed in the capillary body 10, such that in this embodiment too, a fluid connection is provided between the two partial spaces 21 and 22 by means of a capillary 23.

By inserting a distance ring 9a, all deviations from the corresponding desired values arising in the transmission link from the pressure spring 8 to the driven piston 6 can be simply compensated for. In this way, not only differences in the pressure springs but also for example capillary defects may be compensated for by means of the distance ring 9a. Compensating is achieved by setting the bias of the pressure spring 8 by means of an easily replaceable distance ring 9a. There are thus distance rings 9a of various strengths for various types of devices, and when the device is being assembled, the distance ring which exhibits the optimal strength for compensating is inserted.

The functionality of the infusion device will now be described:

In the state shown in FIG. 1, the container 1 is filled with the product and the delivering piston 2 correspondingly assumes its distal position in the container 1. The driven piston 6 also correspondingly assumes its distal position in the inner sleeve 4b. In this distal position, the driven piston 6 is ideally occluded by the rear front area of the inner sleeve 4b, in order to keep the overall length of the device as short as possible.

In this state of the device, the partial fluid space 22 exhibits its smallest volume. The partial fluid space 23 correspondingly exhibits its largest volume. The driven piston 6 is held in its distal position either directly by the user or preferably by means of a latch. At the same time, the drive piston 5 assumes its proximal position. In this proximal position of the drive piston 5, the pressure spring 8 is tensed between the two areas formed by the collar area of the drive piston 5 and the distance ring 9a.

For subcutaneously administering the product, an injection needle arranged at the proximal end of the catheter 20 is inserted, and the latch on the driven piston 6 or the piston rod 7 respectively is released. Under the pressure of the pressure spring 8, a fluid pressure is built up in the partial fluid space 21 via the drive piston 5. This fluid pressure can only be decreased by the capillary 23. Under the pressure of the drive piston 5, fluid flows out of the partial fluid space 21, through the capillary 23, into the partial fluid space 22. The driven piston 6 is moved in the proximal direction by the pressure building in the partial fluid space 22. The partial fluid space 21 thus forms a drive side and the partial fluid space 22 a driven side of the fluid space 21, 22 as a whole. More precisely, the drive side is formed by a piston area of the drive piston 5 facing the partial fluid space 21, and the drive side by a piston area of the driven piston 6 facing the partial fluid space 22.

In the example embodiment, a pressure reducing means is formed by the capillary body 10, the outer sleeve 3 and the capillary 23 formed by their co-operation. A constructively determined drop in pressure is effected by said pressure reducing means. Due to the drop in pressure generated, it is possible to use a stronger pressure spring 8 for driving the delivering piston 2 than would be possible in an unchoked drive.

Moreover, the piston area of the drive piston 5 is larger than the piston area of the driven piston 6. Correspondingly, a stroke of the drive piston 5 effects a comparatively greater stroke of the driven piston 6. The driven piston 6 in turn acts directly on the delivering piston 2 by means of the rigid piston rod 7. Correspondingly, a complete stroke of the driven piston 6 corresponds to the stroke of the delivering piston 2. The stroke of the delivering piston 2 is in turn determined by the conventionally used containers 1. The complete working stroke of the delivering piston 2, which corresponds to a complete delivery of the contents of the container 1, compares with a by comparison substantially shorter working stroke of the drive piston 5 and thus of the pressure spring 8.

The concentric arrangement of the two partial fluid spaces 21 and 22 of the overall fluid space 21, 22 is also constructively interesting. Through this arrangement, the overall length of the device can be kept short.

To drive it, the delivering piston 2 is charged with a pressure of about one bar, i.e. it exerts such a pressure on the contents of the container 1. The fluid coupling is correspondingly formed to transmit the force of the pressure spring 8 from the drive side of the fluid space 21, 22 onto the driven side. This is substantially achieved by the pressure reducing means formed by the outer sleeve 3, the capillary body 10 and the capillary 23, and by the size ratio of the two piston areas of the pistons 5 and 6.

After the product has been delivered, for example after the device has been completely emptied, the container 1 can be re-filled to administer product again, or preferably replaced with a new, filled container. Before replacing the container, the delivering piston 2 is retracted by means of the piston rod 7 to the starting position shown in FIG. 1. In the starting position, the piston rod 7 is latched by a suitable locking means. In the course of retracting, the driven piston 6 pushes the fluid out of the completely filled partial fluid space 22 into the partial fluid space 21. In this way, the fluid flows out of the internal space of the inner sleeve 4b, through the opening 14 in the base of the capillary body 10, and via a small intermediate space between the sealing cap 19 and the capillary body 10 to the reflux valve 11, 12, 13. Under the pressure of the fluid in the partial fluid space 22, the reflux valve opens and the fluid flows through the through-flow formed by the reflux valve and into the partial fluid space 21. Here, the pressure of the pressure spring 8 has to be overcome to advance the drive piston 5 in the proximal direction and ultimately into the starting position shown. The device is then ready to deliver product again.

In the foregoing description a preferred embodiment of the invention has been presented for the purpose of illustration and description. It is not intended to be exhaustive or to limit the invention to the precise form disclosed. Obvious modifications or variations are possible in light of the above teachings. The embodiment was chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

List of Reference Numerals

| | |
|---|---|
| 1 | container, ampoule |
| 2 | delivering means, delivering piston |
| 3 | casing, outer sleeve |
| 4a | container holder |
| 4b | inner sleeve |
| 5 | drive piston |
| 6 | driven piston |
| 7 | piston rod |
| 8 | drive means, drive spring, pressure spring |
| 9 | sealing cap |
| 9a | distance piece |
| 10 | separating body, capillary body |
| 11 | valve ball |
| 12 | valve spring |
| 13 | valve closure |
| 14 | aperture opening |
| 15 | sealing rings |
| 16 | sealing rings |
| 17 | sealing rings |
| 18 | sealing ring |
| 19 | sealing cap |
| 20 | catheter |

-continued

| | |
|---|---|
| 21 | partial fluid space |
| 22 | partial fluid space |
| 23 | fluid connection, system of capillaries, fluid channel, capillary |

What is claimed is:

1. A device for administering an injectable product, comprising:
   a) a casing;
   b) a container for the product accommodated by said casing;
   c) a delivering means for delivering product out of said container;
   d) a drive means; and
   e) a transmission link via which said drive means drives said delivering means, said transmission link comprising a fluid space for an incompressible fluid and a pressure reducing means, wherein said fluid space can be impinged on a drive side by pressure from said drive means and said pressure reducing means reduces a fluid pressure generated by said drive means toward a driven side of said fluid space.

2. The device as set forth in claim 1, wherein a working stroke of said drive means is transmitted in said fluid space into a working stroke of said delivering means which is greater than the working stroke of said drive means.

3. The device as set forth in claim 2, wherein a bias of said drive means is determined by a distance ring.

4. The device as set forth in claim 1, wherein said drive side of said fluid space is formed by a piston area of a drive piston which is larger than a piston area of a driven piston which forms the driven side of said fluid space.

5. The device as set forth in claim 1, wherein said fluid space is sub-divided into a first partial space including said drive side and a second partial space including said driven side, and in that said two partial spaces are connected to each other by a fluid connection formed by said pressure reducing means.

6. The device as set forth in claim 5, wherein said two partial spaces are connected to each other by a system of capillaries, if a higher pressure prevails in said first partial space than in said second partial space.

7. The device as set forth in claim 5, wherein said fluid connection includes a generally spiral fluid channel.

8. The device as set forth in the claim 7, wherein said pressure reducing means comprises a capillary body, and said spiral fluid channel is formed between a surface area of said capillary body and an adjacent surface area.

9. A The device as set forth in claim 5, wherein one of said first partial space and said second partial space is formed as a toroidal chamber between an outer sleeve and an inner sleeve, and the other of said two partial spaces is formed in said inner sleeve.

10. The device as set forth in the claim 9, wherein said toroidal chamber forms said first partial space, and a drive piston guided fluid-proof by said outer sleeve and said inner sleeve forms said drive side.

11. A device for administering an injectable product, comprising:
   a generally cylindrical outer sleeve;
   an inner sleeve generally concentric with the outer sleeve and housing a driven piston;
   a ring space generally between the outer sleeve and the inner sleeve and housing a drive piston and a spring;

the outer and inner sleeves and the driven and drive pistons substantially defining a fluid space;

a capillary body in the fluid space and substantially separating the fluid space into a first partial space and a second partial space; and at least one capillary generally defined by the capillary body and operably linking the first and second partial spaces.

12. The device according to claim 11, further comprising a one-way valve in the capillary body.

13. The device according to claim 11, wherein the spring urges the drive piston to initially pressurize one of the first and second partial spaces, thereby pressurizing the other of the partial spaces through the at least one capillary and causing the driven piston to move.

14. The device according to claim 11, wherein the drive and driven pistons each have a piston area, and wherein the drive piston has a larger piston area that of the driven piston.

15. The device according to claim 11, wherein the drive and driven pistons each have a stroke, the stroke of said drive piston less than that of the driven piston.

16. A device for administering an injectable product comprising:

means for delivering;

means for driving the means for delivering; and a fluid coupling operably coupling the means for driving and means for delivering, whereby the energy produced by the means for driving is attenuated.

17. The device according to claim 16, wherein the energy produced by the means for driving is attenuated and applied evenly to the means for delivering.

18. The device according to claim 16, wherein the fluid coupling comprises a capillary.

19. The device according to claim 16, wherein the means for driving comprises a partial space containing a fluid and a piston for pressurizing the fluid in the partial space, and the means for delivering comprises another partial space and a piston for acting on the injectable product.

20. The device according to claim 18, said fluid coupling operably coupling the partial space and the another partial space.

21. The device according to claim 19, wherein the pistons each have an associated piston area, the piston area of the piston of the means for driving being larger than the piston area of the piston of the means for delivering.

22. The device according to claim 19, wherein the partial space and the another partial space are generally concentric.

* * * * *